(12) United States Patent
Sharma et al.

(10) Patent No.: US 11,918,278 B2
(45) Date of Patent: Mar. 5, 2024

(54) MEDICAL DELIVERY SYSTEMS AND METHODS OF USING THE SAME

(71) Applicant: Boston Scientific Medical Device Limited, Galway (IE)

(72) Inventors: Deepak Kumar Sharma, Muzaffarnafar (IN); Hitendra Purohit, Vadodara (IN); Agrim Mishra, New Delhi (IN)

(73) Assignee: BOSTON SCIENTIFIC MEDICAL DEVICE LIMITED, Galway (IE)

( * ) Notice: Subject to any disclaimer, the term of this patent is extended or adjusted under 35 U.S.C. 154(b) by 234 days.

(21) Appl. No.: 17/323,634

(22) Filed: May 18, 2021

(65) Prior Publication Data

US 2021/0361342 A1    Nov. 25, 2021

Related U.S. Application Data

(60) Provisional application No. 63/027,143, filed on May 19, 2020.

(51) Int. Cl.
| | | |
|---|---|---|
| *A61B 18/14* | (2006.01) | |
| *A61M 1/00* | (2006.01) | |
| A61B 18/00 | (2006.01) | |

(52) U.S. Cl.
CPC .............. *A61B 18/14* (2013.01); *A61M 1/96* (2021.05); *A61B 2018/00214* (2013.01); *A61B 2018/00595* (2013.01); *A61B 2018/00916* (2013.01); *A61B 2018/144* (2013.01); *A61B 2218/007* (2013.01); *A61M 2205/12* (2013.01)

(58) Field of Classification Search
CPC .............. A61B 17/0057; A61B 18/14; A61B 2017/00623; A61B 2017/00884; A61B 2018/00214; A61B 2018/00595; A61B 2018/00916; A61B 2018/144; A61B 2218/007; A61M 1/96; A61M 2205/12
USPC .......................................................... 606/46
See application file for complete search history.

(56) References Cited

U.S. PATENT DOCUMENTS

| | | | |
|---|---|---|---|
| 5,507,744 A  * | 4/1996 | Tay .................... | A61B 17/0057 606/41 |
| 5,653,684 A  * | 8/1997 | Laptewicz ................ | A61F 2/90 606/41 |
| 6,610,026 B2 | 8/2003 | Cragg et al. | |
| 7,175,646 B2 | 2/2007 | Brenneman et al. | |

(Continued)

OTHER PUBLICATIONS

International Search Report and Written Opinion in International Application No. PCT/IB2021/054279, dated Aug. 30, 2021 (12 pages).

*Primary Examiner* — Michael F Peffley
(74) *Attorney, Agent, or Firm* — Bookoff McAndrews, PLLC (57) ABSTRACT

A medical device that includes a handle, a shaft extending distally from the handle and defining a lumen, and an actuator disposed in the shaft and including a distal tip. The actuator and the distal tip are movable relative to the lumen. The medical device includes an expandable member having an inner cavity. The actuator is configured to engage the expandable member when moving distally relative to the lumen and in response to the distal tip entering the inner cavity. The actuator is configured to disengage the expandable member when moving proximally relative to the lumen and in response to the distal tip exiting the inner cavity.

20 Claims, 7 Drawing Sheets

(56) References Cited

U.S. PATENT DOCUMENTS

| | | | |
|---|---|---|---|
| 7,833,278 B2 * | 11/2010 | Evans | A61F 2/4618 |
| | | | 623/23.61 |
| 8,080,032 B2 * | 12/2011 | van der Burg | A61B 17/12136 |
| | | | 606/200 |
| 8,425,552 B2 | 4/2013 | Zhu et al. | |
| 9,095,342 B2 * | 8/2015 | Becking | A61B 17/12109 |
| 9,364,205 B2 | 6/2016 | Zhu et al. | |
| 10,076,335 B2 * | 9/2018 | Zaver | A61B 17/12172 |
| 2009/0234380 A1 | 9/2009 | Gabel et al. | |
| 2010/0106068 A1 | 4/2010 | Karpiel et al. | |
| 2010/0312259 A1 | 12/2010 | Houser et al. | |
| 2012/0191129 A1 | 7/2012 | Kerber | |
| 2014/0330309 A1 | 11/2014 | Gonzalez et al. | |
| 2015/0148785 A1 | 5/2015 | Kleiner | |
| 2019/0365385 A1 * | 12/2019 | Gorochow | A61B 17/12168 |

* cited by examiner

MEDICAL DELIVERY SYSTEMS AND METHODS OF USING THE SAME

CROSS-REFERENCE TO RELATED APPLICATIONS

This application claims the benefit of priority from U.S. Provisional Application No. 63/027,143, filed on May 19, 2020, which is incorporated by reference herein in its entirety.

TECHNICAL FIELD

Various aspects of the disclosure relate generally to medical delivery systems, devices, and related methods. Examples of the disclosure relate to systems, devices, and related methods for delivering a medical tool relative to a subject, among other aspects.

BACKGROUND

Endoscopic and open surgical procedures of the gastrointestinal (GI) tract include, for example, colonic resection, bariatric surgery, esophagectomy, gastric bypass, and sleeve gastrectomy, among others. These procedures may result in perforation, post-surgical leaks, or other wounds of the tract. Limited treatment options exist for managing such wounds, which have significant morbidity and mortality rates. Options include surgical re-operation and endoscopic placement of a stent or clips. Surgery is relatively invasive and also has high morbidity and mortality rates. Endoscopic stent placement is a less invasive option. The placed stent, however, can migrate from the intended location and/or wall off infection at the treatment site, inhibiting drainage.

SUMMARY

Aspects of the disclosure relate to, among other things, systems, devices, and methods for treating a target treatment site using negative pressure with one or more expandable members, among other aspects. Each of the aspects disclosed herein may include one or more of the features described in connection with any of the other disclosed aspects.

According to an example, a medical device includes a handle, a shaft extending distally from the handle and defining a lumen, and an actuator disposed in the shaft and including a distal tip. The actuator and the distal tip are movable relative to the lumen. The medical device includes an expandable member having an inner cavity. The actuator is configured to engage the expandable member when moving distally relative to the lumen and in response to the distal tip entering the inner cavity. The actuator is configured to disengage the expandable member when moving proximally relative to the lumen and in response to the distal tip exiting the inner cavity.

Any of the medical devices described herein may include any of the following features. A distal portion of the shaft is tapered such that a dimension of the lumen increases at the distal portion. The medical device includes an actuator body movably coupled to an exterior of the handle and disposed over a slot of the handle. A proximal portion of the actuator is received within the slot and fixed to the actuator body such that translation of the actuator body relative to the slot is configured to move the actuator relative to the lumen of the shaft. The shaft is configured to receive the expandable member within the lumen when the distal tip is received within the inner cavity and the actuator is moved proximally relative to the lumen. The distal portion of the shaft is configured to maintain the expandable member in a compressed state, and permit the expandable member to transition to an expanded state in response to the actuator moving distally relative to the lumen and the expandable member extending outward from the shaft. The distal portion of the shaft is configured to remove the distal tip from the inner cavity in response to the distal portion of the shaft engaging a proximal end of the expandable member when the actuator moves proximally relative to the lumen. The medical device includes a cautery device extending distally from the shaft, wherein the cautery device is configured to cauterize tissue. The cautery device defines an inner channel that is tapered such that a dimension of the inner channel increases distally from the shaft. The expandable member includes an opening such that the inner cavity is accessible via the opening. The actuator includes an inner channel extending between a proximal end and the distal tip. The medical device includes a negative pressure source coupled to the proximal end of the actuator and in fluid communication with the distal tip through the inner channel. The negative pressure source is configured to generate a negative pressure through the inner channel such that fluid positioned adjacent to the expandable member is drawn through the expandable member and into the inner channel via the distal tip. The medical device includes a cassette including a first channel and a second channel, wherein the cassette is configured to hold the expandable member in the second channel. The first channel is in coaxial alignment with the second channel and includes a diameter greater than the second channel. The cassette is configured to receive the shaft within the first channel and the distal tip within the second channel. The cassette is configured to inhibit the shaft from extending into the second channel.

According to another example, a medical device includes a handle having a movable actuator body, a shaft extending distally from the handle, and an actuator wire disposed within the shaft. The movable actuator body is configured to translate the actuator wire out of the shaft to insert the actuator wire into an expandable member, when the actuator wire moves along the handle in a first direction. The movable actuator body is configured to translate the actuator wire into the shaft to remove the actuator wire from inside the expandable member, when the actuator wire moves along the handle in a second direction that is opposite of the first direction.

Any of the medical devices described herein may include any of the following features. The shaft is configured to receive the expandable member in a compressed state when the actuator wire is inserted into the expandable member and the movable actuator body is moved in the second direction. The medical device includes a cautery device extending distally from the shaft, wherein the cautery device is configured to generate heat to cauterize tissue. The cassette is configured to receive the shaft within the first channel and the actuator wire within the second channel. The cassette is configured to inhibit the shaft from extending into the second channel.

According to another example, a medical device includes a handle, a shaft extending distally from the handle, and an actuator including a wire disposed within the shaft. The medical device includes a cassette including a channel housing an expandable member. The actuator is configured to extend the wire outwardly from the shaft and into the cassette to engage the expandable member within the channel, when the actuator moves distally over the shaft. The actuator is configured to retract the wire into the shaft and outward from the cassette to remove the expandable member from the channel, when the actuator moves proximally over the shaft.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary aspects of the disclosure and together with the description, serve to explain the principles of the disclosure.

DETAILED DESCRIPTION

Endoluminal vacuum therapy (EVAC) has been proposed. In EVAC, negative pressure is delivered to a target area (e.g., a wound site or cyst) in the GI tract, for example through a nasogastric tube having a sponge at its terminal end. The sponge is placed endoscopically into a perforation, leak, or other wound at the target area. Negative pressure then is applied. Devices and systems suited for EVAC are limited, however.

Examples of the disclosure include systems, devices, and methods for removing materials from a target site within a subject (e.g., patient) by generating a negative pressure therein. Examples of the disclosure further include devices, systems, and methods for closing a perforation or other wound. In examples, EVAC includes endoluminal placement of a porous body, e.g., a sponge, a foam, or other like material into the wound site, including a perforation, a cyst, a leak, an anastomosis, etc. Placement of the material may be via a catheter, scope (endoscope, bronchoscope, colonoscope, etc.), tube, or sheath, inserted into the GI tract via a natural orifice. The orifice can be, for example, the nose, mouth, or anus, and the placement can be in any portion of the GI tract, including the esophagus, stomach, duodenum, large intestine, or small intestine. Placement also can be in other organs reachable via the GI tract.

Reference will now be made in detail to aspects of the disclosure, examples of which are illustrated in the accompanying drawings. Wherever possible, the same or similar reference numbers will be used through the drawings to refer to the same or like parts. The term "distal" refers to a portion farthest away from a user when introducing a device into a patient. By contrast, the term "proximal" refers to a portion closest to the user when placing the device into the subject. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." As used herein, the terms "about," "substantially," and "approximately," indicate a range of values within +/−10% of a stated value.

Examples of the disclosure may relate to devices and methods for performing various medical procedures and/or treating portions of the large intestine (colon), small intestine, cecum, esophagus, any other portion of the gastrointestinal tract, and/or any other suitable patient anatomy (collectively referred to herein as a "target treatment site"). Various examples described herein include single-use or disposable medical devices.

Figure 1:
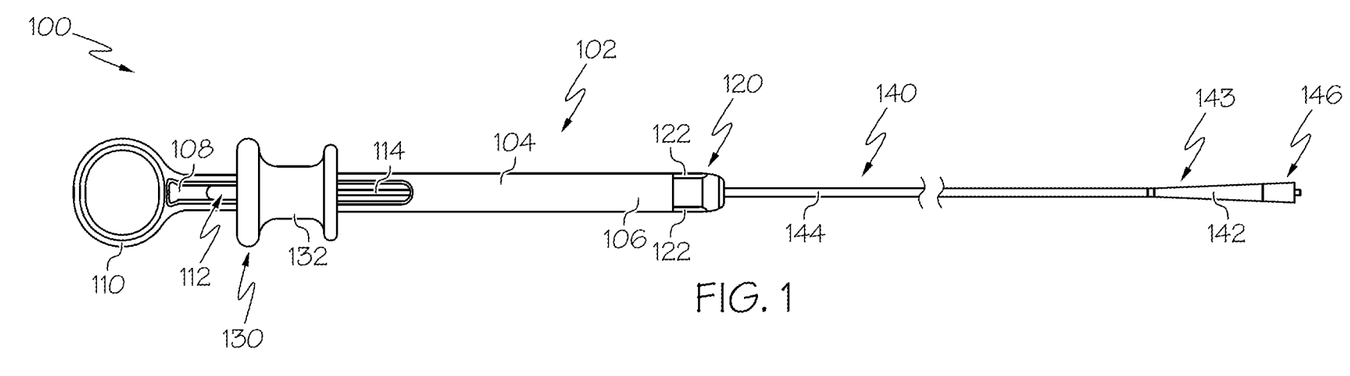
FIG. 1 is a perspective view of an exemplary medical device including a handle and a shaft, according to aspects of this disclosure.

FIG. 1 shows an exemplary medical device 100 in accordance with an example of this disclosure. Medical device 100 may include a handle 102, an actuation wire 114, an actuator 130, and a shaft 140. Handle 102 may include a body 104 having a longitudinal length defined by a distal end 106 and a proximal end 108. Handle 102 may define one or more lumens extending through body 104 between distal end 106 and proximal end 108. Handle 102 may further include a grasping feature 110 at proximal end 108 that is configured to be manually grasped by a user of medical device 100. In the example, grasping feature 110 may include a ring positioned proximal to proximal end 108 and that is sized and/or shaped to receive a digit of a user therethrough (e.g., a thumb, etc.).

Handle 102 may further include a slot 112 disposed through at least a portion of body 104, such as between distal end 106 and proximal end 108. Slot 112 is configured to receive at least a portion of actuator 130 therein. As described further herein, actuator 130 may be movable relative to handle 102, and slot 112 may define a travel path and/or a stroke length of actuator 130 along handle 102. Handle 102 may be configured to receive actuation wire 114 through at least one lumen of body 104 (e.g., a working lumen) via slot 112. Accordingly, it should be understood that at least a portion of actuation wire 114 (e.g., a proximal portion) may be received within slot 112. Actuation wire 114 may be fixed to actuator 130 within slot 112 such that movement of actuator 130 relative to handle 102 (and slot 112) provides a simultaneous and corresponding movement of actuation wire 114 through slot 112 and a working lumen of body 104.

Still referring to FIG. 1, actuator 130 may include a spool 132 defining a body of actuator 130, with spool 132 having an ergonomic configuration that is configured to be manually grasped by a user of medical device 100. In the example, spool 132 may include one or more curvatures and/or surfaces providing an intuitive interface for controlling medical device 100. For example, spool 132 may be sized and shaped to receive one or more fingers of a user thereon (e.g., a forefinger, a middle finger, etc.). Actuator 130 further defines a channel extending through spool 132, the channel being configured to receive body 104 therethrough. Thus, actuator 130 may be disposed about handle 102.

Actuator 130 may be operable to reciprocally translate along body 104 in one or more directions A (e.g., proximally, distally, etc.) in response to a manual actuation of actuator 130 relative to handle 102. In some examples, actuator 130 may translate actuation wire 114 relative to shaft 140 in response to translation of spool 132 along handle 102. Further, actuator 130 may be operable to rotate about body 104 in one or more directions (e.g., clockwise, counter clockwise, etc.). In some examples, actuator 130 may articulate a distal portion of actuation wire 114 to deflect and/or bend a distal portion of shaft 140 in response to rotation of spool 132 about handle 102.

Handle 102 may further include an end cap 120 at distal end 106. End cap 120 may include one or more ridges 122 disposed along an exterior surface of end cap 120 for facilitating a manual manipulation of end cap 120. For example, end cap 120 may be selectively coupled to distal end 106 in response to a rotation of end cap 120 relative to body 104. In some embodiments, end cap 120 may be secured to distal end 106 via an adhesive, a heat shrink, a snap-fit connection, a threaded coupling, a welding, and the like. It should be appreciated that end cap 120 may be securely fixed to handle 102 (i.e. irremovable) upon attachment to body 104. End cap 120 may be formed of plastic, acrylic, metal, and various other suitable materials.

Still referring to FIG. 1, shaft 140 may extend distally from end cap 120 and may include a longitudinal length defined between a distal end 142 and a proximal end 144. End cap 120 may be configured to fix proximal end 144 of shaft 140 to distal end 106 of handle 102 by, for example, an adhesive, a heat shrink, a snap-fit connection, a threaded coupling, a crimping connection, and the like. Shaft 140 may define one or more lumens extending between distal end 142 and proximal end 144. It should be appreciated that at least one lumen of shaft 140 (e.g., a working lumen) may extend parallel to and be in coaxial alignment with at least one lumen of handle 102 (e.g., a working lumen) when shaft 140 is coupled to body 104 via end cap 120. Accordingly, the working lumen of shaft 140 may receive actuation wire 114 therethrough from the working lumen of handle 102.

Shaft 140 may generally include a relative stiffness. In some examples, shaft 140 may be at least partially flexible. Shaft 140 may be formed of Polytetrafluoroethylene (PTFE) and include a plurality of braids (e.g., with reflow) to provide additional stiffness. In the example, shaft 140 may further include a tapered section 143 along a portion of shaft 140 proximate to distal end 142.

Figure 3:
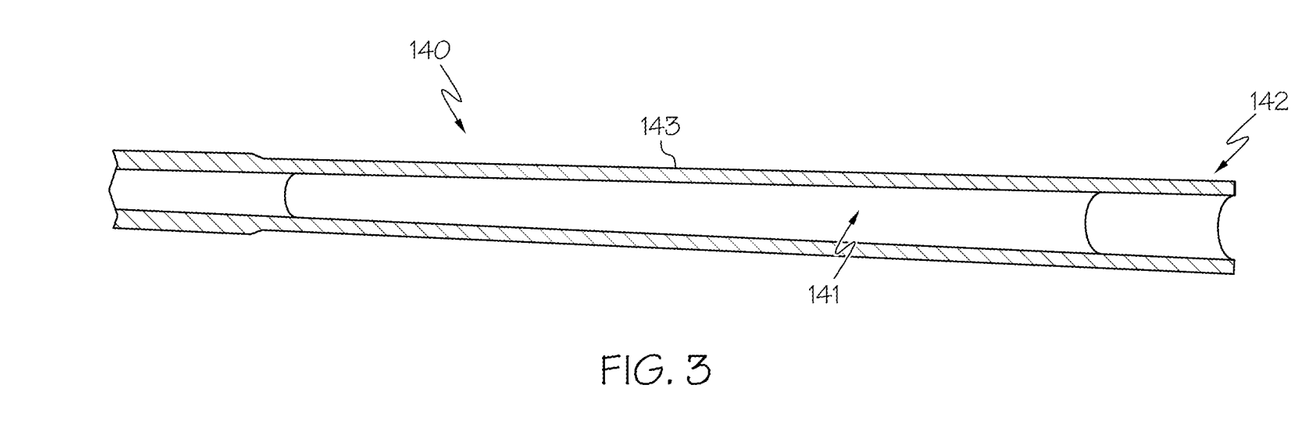
FIG. 3 is a cross-sectional side view of the shaft of the medical device of FIG. 1, according to aspects of this disclosure.

As seen in FIG. 3, tapered section 143 may extend along a predefined length of shaft 140 and may include a greater cross-sectional dimension than a remaining longitudinal length of shaft 140. Further, a diameter of shaft 140 along tapered section 143 may increase along the predefined length of tapered section 143 (e.g., toward distal end 142). Tapered section 143 may be sized and shaped in accordance with a configuration of one or more components of medical device 100 (e.g., an expandable member 160) to facilitate receipt of the component into shaft 140. For example, tapered section 143 may have a diameter ranging from about 1.25 millimeters to 1.75 millimeters, such as 1.50 millimeters. As alluded to above, shaft 140 may define a lumen 141 extending between distal end 142 and proximal end 144. Consequently, it should be appreciated that a cross-sectional dimension (e.g., diameter) of lumen 141 also may increase along tapered section 143 and toward distal end 142.

In some examples, distal end 142 and/or tapered section 143 may be configured to flexibly bend relative to proximal end 144, such as, for example, in response to an articulation of actuation wire 114 disposed in shaft 140. For example, actuation wire 114 may articulate in one or more directions, including, but not limited to, a pair of lateral/horizontal directions relative to a longitudinal axis of shaft 140 (e.g., left, right, etc.), a pair of vertical directions relative to a longitudinal axis of shaft 140 (e.g., up, down, etc.), and the like. In some embodiments, shaft 140 may include an echogenic marker disposed along distal end 142 and/or tapered section 143. In this instance, shaft 140 may be visible when disposed within a subject (e.g., a patient) with use of an imaging device, such as, for example, an endoscopic ultrasound (EUS) system.

Referring back to FIG. 1, medical device 100 may include a cautery device 146 at distal end 142. Cautery device 146 may be configured to cauterize (or otherwise cut) one or more materials (e.g., tissue) and/or objects positioned adjacent to distal end 142, such as, for example, tissue. In the example, cautery device 146 may be coupled to an electrical energy source (not shown) via one or more wires extending through corresponding lumens of handle 102 and shaft 140 (e.g., electrocautery lumens). Accordingly, the electrical energy source is operable to transmit electrical current to cautery device 146 via the one or more wires. It should be appreciated that the electrocautery lumens of handle 102 and shaft 140 may be insulated from one or more other lumens of handle 102 and shaft 140, respectively, such as, the working lumens including actuation wire 114 disposed therein.

Figure 2:
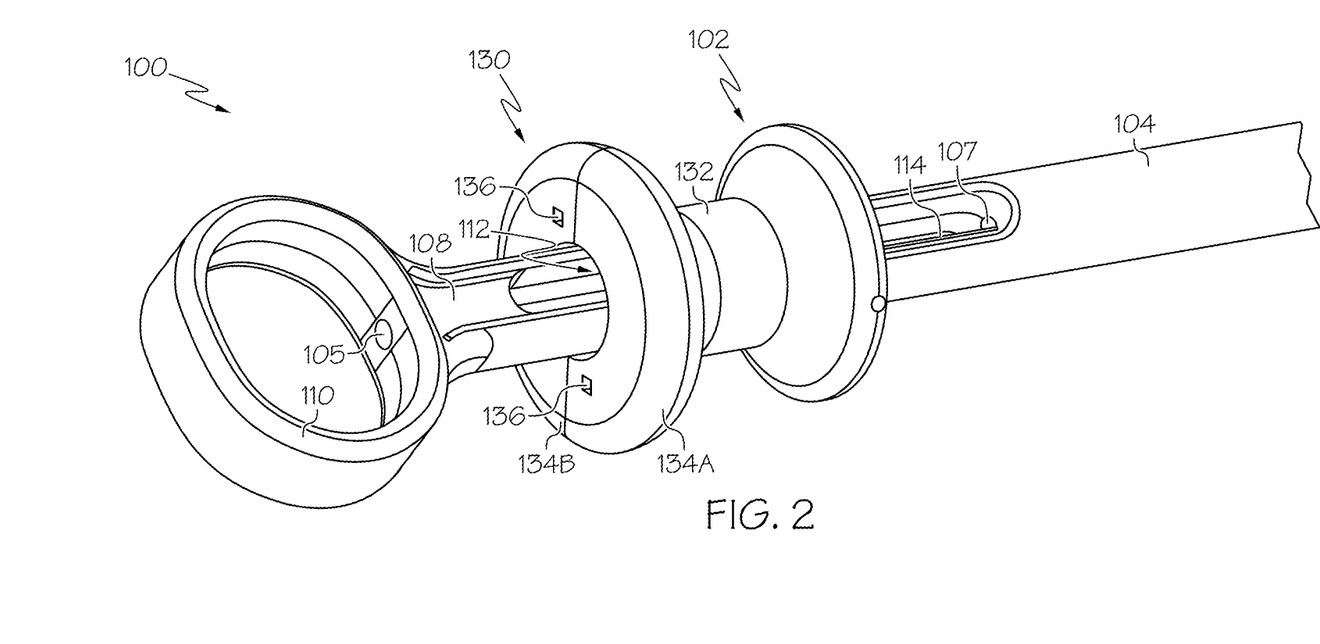
FIG. 2 is a partial perspective view of the handle of the medical device of FIG. 1, according to aspects of this disclosure.

Referring now to FIG. 2, handle 102 is depicted with a pair of openings 105, 107 positioned along body 104. For example, handle 102 may include a first opening 105 at proximal end 108, such as on grasping feature 110. First opening 105 may provide access to a channel extending through proximal end 108 and into a proximal end of slot 112. First opening 105 may be sized and shaped to receive one or more devices therethrough for entry into slot 112 and/or body 104, such as, for example, actuation wire 114, a suction tube, a wire, etc. Handle 102 may further include a second opening 107 at a distal end of slot 112 that provides access to one or more lumens of body 104 (e.g., a working lumen, an electrocautery lumen, etc.).

In the example, actuation wire 114 is received through second opening 107 and into the working lumen of handle 102. Further, actuation wire 114 may include an inner channel sized and shaped to receive one or more devices. For example, referring to FIG. 4, actuation wire 114 may include an opening 119 at a proximal end 118 that is configured to receive the one or more devices, such as, for example, a tube, a conduit, a pressure regulator, etc. Actuation wire 114 may have a longitudinal length defined between proximal end 118 and a distal end 116 such that the one or more devices received at proximal end 118 may extend outwardly from actuation wire 114 at distal end 116. In some examples, proximal end 118 may include a fastening feature (e.g., a threaded portion) for facilitating engagement of actuation wire 114 with the one or more devices (e.g., a conduit, a tube, etc.).

Figure 4:
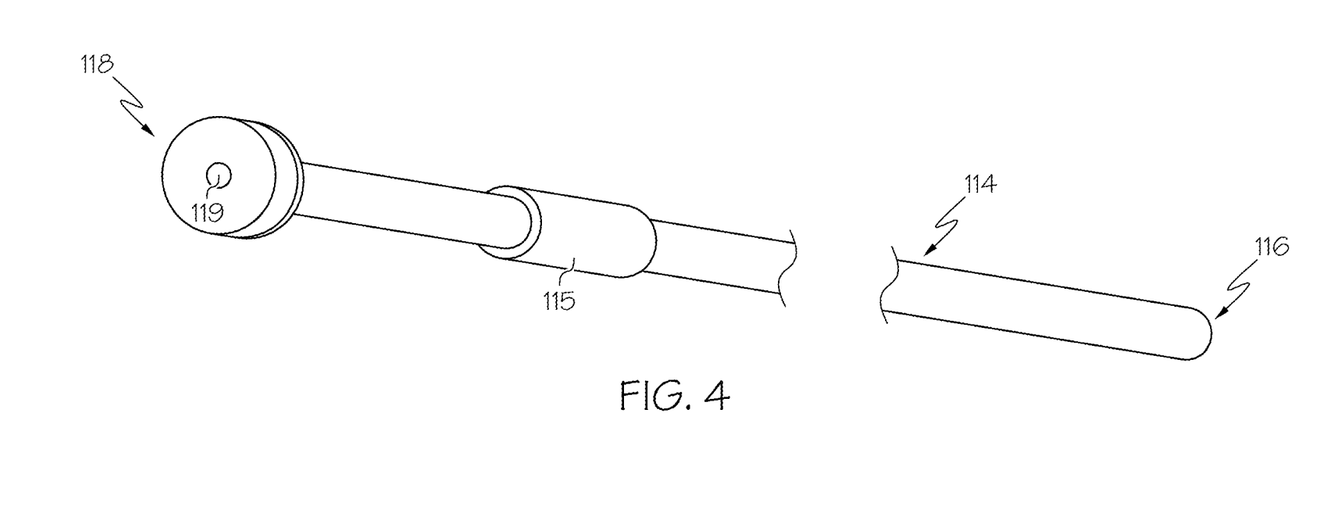
FIG. 4 is a perspective view of an actuation wire of the medical device of FIG. 1, according to aspects of this disclosure.

Actuation wire 114 may further include a sleeve 115 positioned proximate to proximal end 118 and, stated differently, is spaced apart from proximal end 118 such that sleeve 115 is positioned distally relative to proximal end 118. In the example, sleeve 115 is integral with actuation wire 114 and may include a cross-sectional dimension that is relatively greater than a remaining body of actuation wire 114. Sleeve 115 may be configured to engage an interior portion of spool 132 to thereby securely fix actuation wire 114 to actuator 130. For example, sleeve 115 may be received within a slot (not shown) formed along an interior of spool 132, bonded to spool 132 via an adhesive, and the like. It should be understood that actuation wire 114 may include a longitudinal length suitable for positioning proximal end 118 within slot 112 and distal end 116 adjacent to distal end 142. Actuation wire 114 may be formed of stainless steel, Nitinol (i.e., nickel titanium), plastic, aluminum, and the like.

Referring back to FIG. 2, with proximal end 118 fixed to actuator 130 (e.g., at sleeve 115), the one or more devices received through first opening 105 may be further received in the inner channel of actuation wire 114 via opening 119. It should be appreciated that the pair of openings 105, 107 may be positioned along various other suitable portions of body 104 and/or slot 112 than that shown and described herein.

In some embodiments, actuator 130 may include a pair of housings 134A, 134B coupled to one another to form spool 132. Each housing 134A, 134B may include a lock assembly 136 for securing the pair of housings 134A, 134B together. For example, lock assembly 136 may include an aperture disposed along an exterior of each housing 134A, 134B and a protrusion (e.g., a detent, a pin, etc.) that is configured to be received within the aperture of the opposing housing 134A, 134B. Accordingly, it should be appreciated that the pair of housings 134A, 1346 may be selectively engaged (and/or disengaged) to one another to assemble (and/or disassemble) spool 132 onto handle 102 via locking assembly 136. In some examples, locking assembly 136 may provide a snap-fit connection between the pair of housings 134A, 1346 in response to each of the apertures receiving the corresponding protrusion of the opposing housing 134A, 134B.

Figure 5:
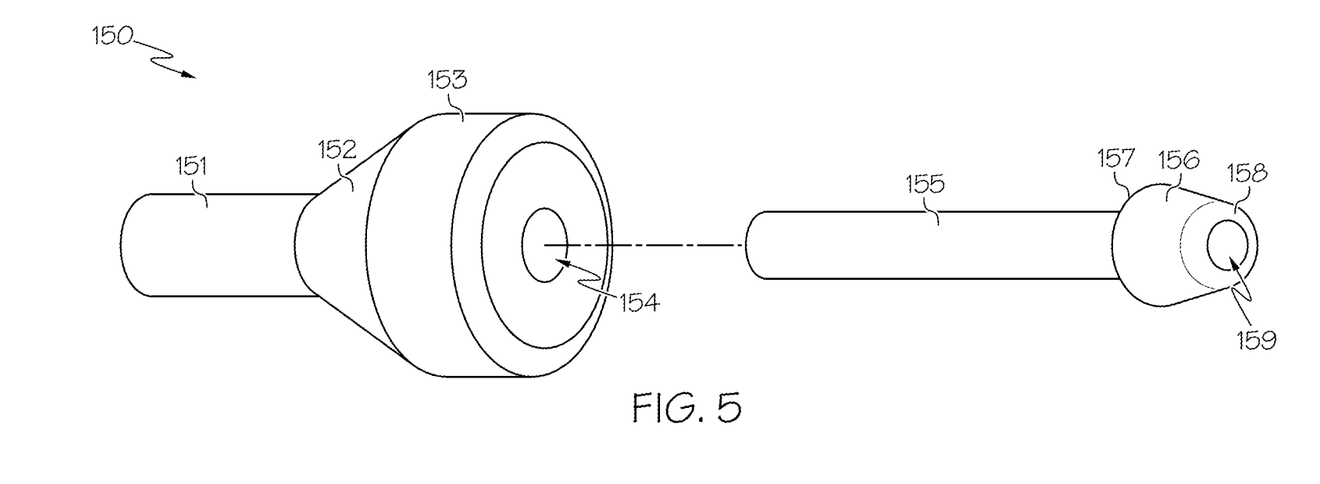
FIG. 5 is a perspective view of an engagement assembly of the medical device of FIG. 1, according to aspects of this disclosure.

Referring now to FIG. 5, medical device 100 may further include an engagement assembly 150 having a proximal base 153, an intermediate body 155, and a distal tip 156. Proximal base 153 and distal tip 156 may be separated from one another by intermediate body 155 positioned therebetween. Accordingly, intermediate body 155 extends distally from proximal base 153, and distal tip 156 extends distally relative to intermediate body 155. In the example, intermediate body 155 may be integral with distal tip 156, and proximal base 153 may be separate from the assembly of intermediate body 155 and distal tip 156. In other examples, proximal base 153 may be integrally formed with intermediate body 155 and distal tip 156. Indeed, the entire engagement assembly 150 may be made from one-piece construction.

Furthermore, proximal base 153 may be integrally formed with a rear body 151 and a tapered body 152, with tapered body 152 extending between proximal base 153 and rear body 151. Stated differently, rear body 151, tapered body 152, and proximal base 153 include a unitary structure; however, in other embodiments one or more of the components may be separate from one another. In the example, rear body 151 may have a cylindrical profile, tapered body 152 may have a conical profile, and proximal base 153 may have a circular profile with a cross-sectional dimension that is greater than the rear body 151. A cross-sectional dimension of tapered body 152 may vary from a distal portion adjacent to proximal base 153 to a proximal portion adjacent to rear body 151.

Still referring to FIG. 5, proximal base 153 may define a distal, planar face opposite of tapered body 152 and rear body 151, with the distal, planar face being sized and/or shaped to facilitate engagement with one or more other components of medical device 100 (e.g., expandable member 160). In the example, proximal base 153 may include an opening 154 along the distal, planar face that is configured to receive intermediate body 155, thereby attaching proximal base 153 to intermediate body 155.

Intermediate body 155 may be securely fixed to proximal base 153 by an adhesive, welding, crimping, ultraviolet (UV) curing, and the like. Intermediate body 155 may have an elongated, cylindrical profile with a constant cross-sectional dimension that is relatively less than proximal base 153. Although not shown, rear body 151 may further include an opening at a proximal end, positioned opposite of tapered body 152, which is in fluid communication with opening 154.

Distal tip 156 may include a rear face 157 and a front face 158, with intermediate body 155 secured to distal tip 156 at rear face 157. In the example, distal tip 156 may include a cross-sectional dimension that is relatively less than proximal base 153 and greater than intermediate body 155. Further, distal tip 156 may have a conical profile such that a cross-sectional dimension of distal tip 156 may gradually decrease between rear face 157 and front face 158. In the example, a cross-sectional dimension of distal tip 156 at rear face 157 may be relatively greater than at front face 158. In other examples, distal tip 156 may include a spherical, square, rectangular, oval, and/or various other suitable profiles.

Still referring to FIG. 5, distal tip 156 may include an opening 159 on front face 158. Opening 159 may provide access to the channel extending through distal tip 156 and intermediate body 155. As described further below, opening 159 may be operable to fluidly couple engagement assembly 150 with one or more components of medical device 100, in response to engagement assembly 150 engaging the component (e.g., expandable member 160). In some embodiments, distal tip 156 may be selectively coupled to intermediate body 155 along rear face 157; while in other embodiments, distal tip 156 may be securely fixed to intermediate body 155 (e.g., by an adhesive, welding, crimping, ultraviolet (UV) curing, etc.).

Figure 9:
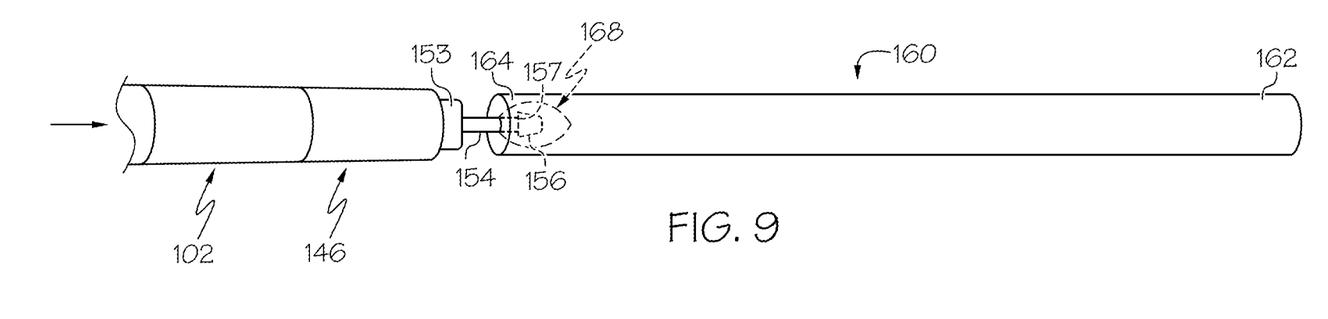
FIG. 9 is a perspective view of the expandable member of FIG. 7 receiving the medical device of FIG. 1 in the inner cavity; according to aspects of this disclosure.

Distal tip 156 may be sized, shaped, and configured to selectively engage expandable member 160 (FIG. 9). It should be appreciated that rear body 151, tapered body 152, proximal base 153, intermediate body 155, and/or distal tip 156 may each include a respective channel such that the various bodies/components of engagement assembly 150 may be in fluid communication with one another when in an assembled state. Thus, opening 159 may be fluidly coupled to the opening at rear body 151 via the channels of engagement assembly 150.

Figure 6:
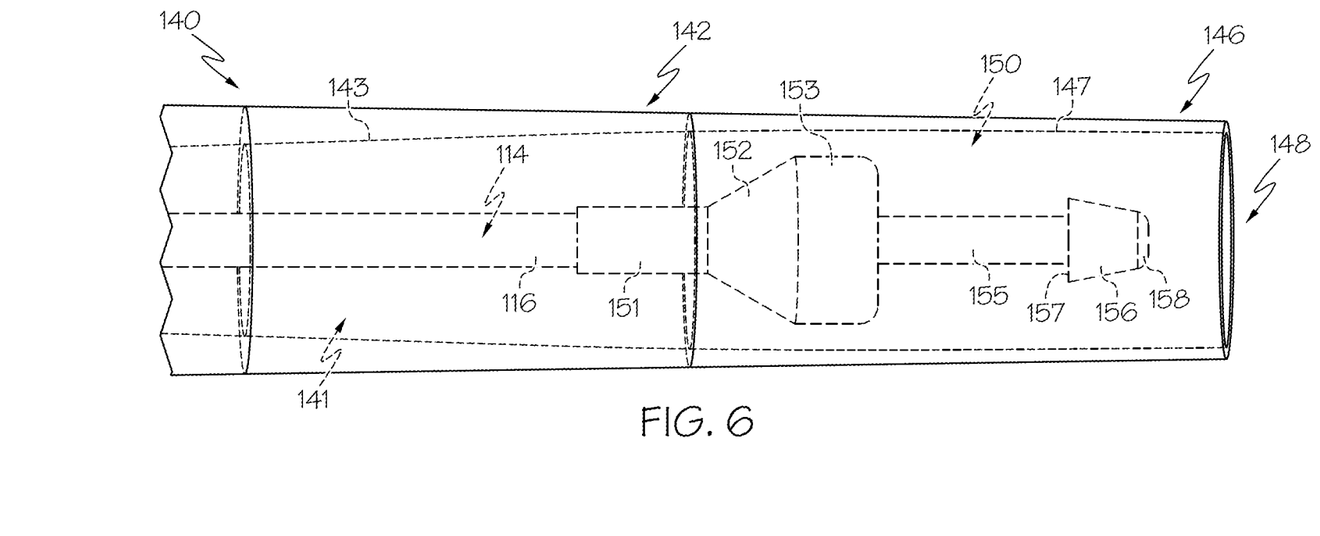
FIG. 6 is a side view of the actuation wire of FIG. 4 and the engagement assembly of FIG. 5 received within the shaft of the medical device of FIG. 1, according to aspects of this disclosure.

Referring now to FIG. 6, distal end 142 and cautery device 146 is shown in a partially transparent manner. Distal end 116 is disposed within lumen 141 at distal end 142. In the example, engagement assembly 150 may be coupled to actuation wire 114. For example, distal end 116 may be received within rear body 151 such that a channel of engagement assembly 150 may be parallel to, and in coaxial alignment with, an inner channel of actuation wire 114. In some examples, actuation wire 114 may be secured to engagement assembly 150 at rear body 151 by an adhesive, welding, crimping, ultraviolet (UV) curing, etc.

Thus, the inner channel of actuation wire 114 may be in fluid communication with opening 159 at distal tip 156 via proximal base 153 and intermediate body 155. In some embodiments, proximal base 153 may be selectively coupled to actuation wire 114 and/or intermediate body 155; while in other embodiments, proximal base 153 may be securely fixed to actuation wire 114 and/or intermediate body 155 (e.g., by an adhesive, welding, crimping, ultraviolet (UV) curing, etc.).

Still referring to FIG. 6, cautery device 146 may include a tapered body 147 such that a cross-sectional dimension of cautery device 146 may vary. In the example, tapered body 147 may include a relatively greater cross-sectional dimension along a proximal portion of cautery device 146 adjacent to distal end 142. As described in further detail herein, tapered body 147 is sized and shaped in accordance with a configuration of expandable member 160 (FIG. 7) to facilitate receipt of expandable member 160 into cautery device 146. For example, tapered body 147 may have a diameter ranging from about 1.25 millimeters to 1.75 millimeters, such as 1.50 millimeters.

Figure 7:
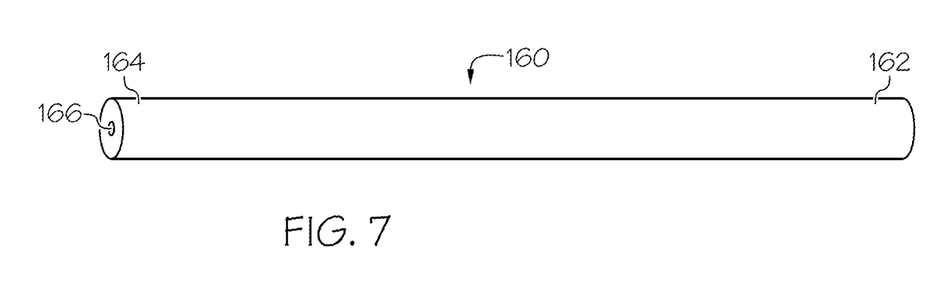
FIG. 7 is a perspective view of an expandable member, according to aspects of this disclosure.

Referring to FIG. 7, expandable member 160 may include a longitudinal length defined between a distal end 162 and a proximal end 164. Expandable member 160 may include various sizes and/or shapes, including, for example, cylindrical, rectangular, oval, square, and/or other suitable shapes. In embodiments of this disclosure, expandable member 160 may include a sponge and/or foam that may be any suitable biocompatible material capable of absorbing liquids and/or permitting liquid to pass therethrough via negative pressure, suction, and/or vacuum. In some embodiments, expandable member 160 may be flexible, compressible, porous, hydrophilic, sterile, and/or disposable. In the example, the expandable member 160 includes an open-cell foam.

Suitable materials of expandable member 160 may include, for example, polyurethanes, esters, ethers, composite materials, absorbing polymer powder, micro/nano-porous materials, and any medical-grade material. Expandable member 160 may be formed of biodegradable materials such that expandable member 160 may be absorbed by tissue when deployed at a target site within a subject (e.g., patient). In some embodiments, expandable member 160 may include an echogenic marker disposed between distal end 162 and proximal end 164. In this instance, expandable member 160 may be visible when disposed within a subject (e.g., a patient) with use of an imaging device, such as, for example, an endoscopic ultrasound (EUS) system.

In the example, expandable member 160 may be configured to transition from a collapsed state (FIG. 7) to an expanded state (FIG. 8) absent a compressing force applied to expandable member 160. Stated differently, expandable member 160 may be naturally configured to expand (e.g., radially, longitudinally, etc.) and form a greater cross-sectional dimension when in a default, unbiased configuration. For example, expandable member 160 may have a diameter ranging from about 1.5 millimeters to about 2.5 millimeters when in the expanded state, such as about 2.0 millimeters. Further, expandable member 160 may have a diameter ranging from about 0.75 millimeters to about 1.25 millimeters when in the collapsed state, such as about 1.0 millimeters.

Still referring to FIG. 7, expandable member 160 may include hole 166 at proximal end 164. In the example, hole 166 is maintained in a first, unexpanded configuration when in a default state. As described further herein, hole 166 may be expanded in response to expandable member 160 receiving an exerting force at proximal end 164, such as, for example, by engagement assembly 150. Hole 166 may be configured to provide access to a cavity 168 of expandable member 160 (FIG. 8).

Figure 8:
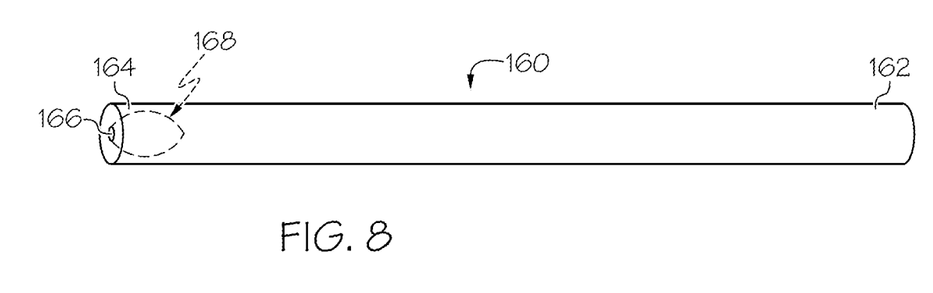
FIG. 8 is a perspective view of the expandable member of FIG. 7 including an inner cavity, according to aspects of this disclosure.

Referring to FIG. 8, cavity 168 may be disposed within expandable member 160 and positioned adjacent to proximal end 164. Cavity 168 may be sized and shaped to receive one or more components of medical device 100 therein, such as, for example, engagement assembly 150. Cavity 168 may include various suitable sizes and/or shapes, including, for example, spherical, oval, cylindrical, square, rectangular, triangular, and/or other suitable shapes. It should be appreciated that cavity 168 may be defined by one or more inner walls of expandable member 160. The one or more inner walls may be expandable and/or collapsible in response to cavity 168 receiving engagement assembly 150 through hole 166 (FIG. 9).

Additionally and/or alternatively, the one or more inner walls may be expandable and/or collapsible in response to expandable member 160 transitioning between the collapsed and expanded states. In other embodiments, distal tip 156 may include a threaded portion and proximal end 164 (and/or cavity 168) may include a corresponding threaded portion. In this instance, engagement assembly 150 may be configured to engage expandable member 160 in response to rotatably coupling the threaded portion of distal tip 156 to the corresponding threaded portion of proximal end 164.

In further embodiments, medical device 100 may omit engagement assembly 150 entirely and distal end 116 may include a disc. The disc may include a distal opening in fluid communication with the inner channel of actuation wire 114. In this instance, the disc may engage expandable member 160 in response to generating a suction through the distal opening, such as, for example, by a negative pressure formed within actuation wire 114 by a pressure regulator. The pressure regulator may be coupled to actuation wire 114 at proximal end 118 (FIG. 4).

Figure 10A:
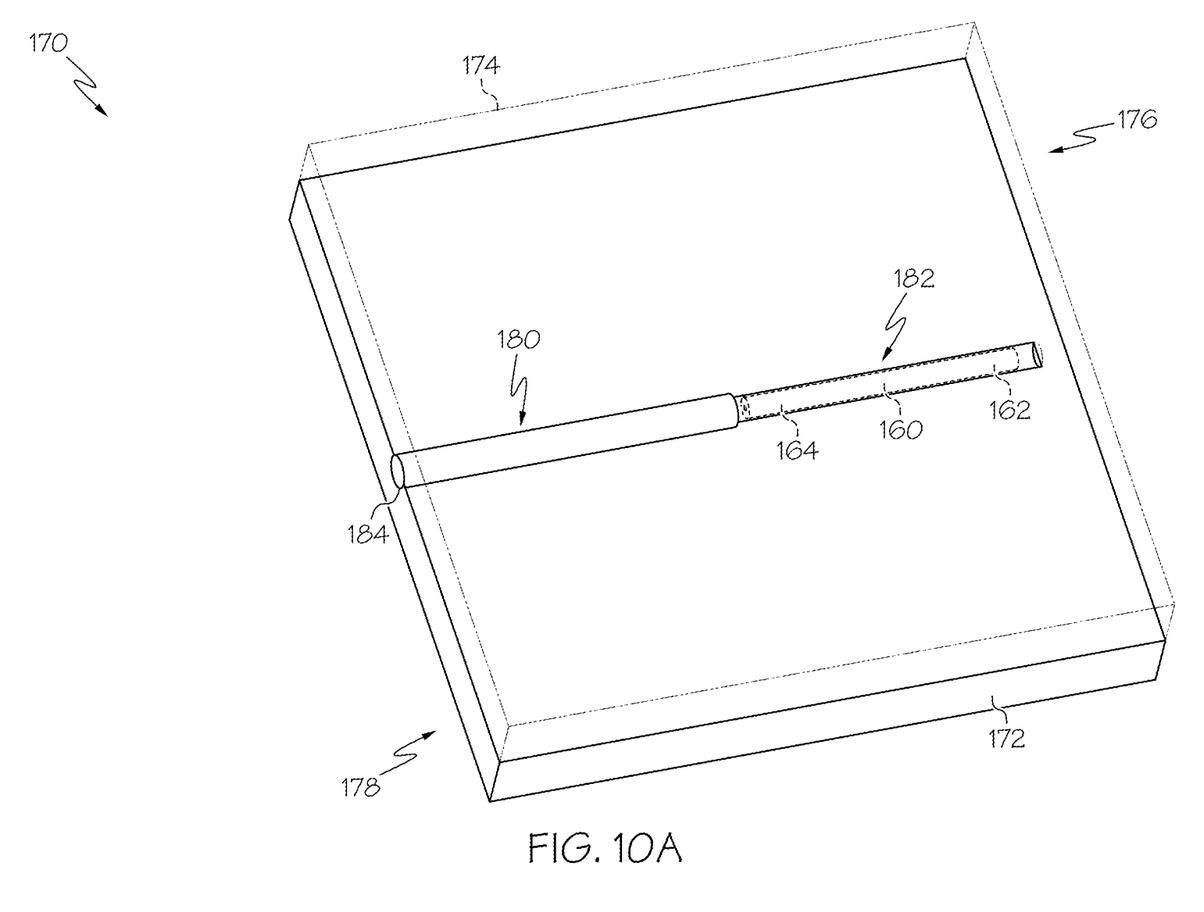
FIG. 10A is a perspective view of an exemplary cassette device including the expandable member of FIG. 7 housed therein, according to aspects of this disclosure.

Referring now to FIG. 10A, a cassette device 170 is shown with expandable member 160 housed therein in a compressed state. Cassette device 170 may define a housing for maintaining expandable member 160 in a compressed and sterile condition prior to use with medical device 100. For example, cassette device 170 may include a bottom wall 172 and a top wall 174 secured to one another along interior surfaces (e.g., via a snap-fit connection, adhesive, molding, welding, etc.). Walls 172, 174 may include various sizes and/or shapes, including, for example, rectangular, square, oval, circular, etc. In some examples, the medical device 100 may include a kit having multiple cassette devices 170 for holding multiple expandable members 160 for use with medical device 100.

In the example, bottom wall 172 may be generally opaque and top wall 174 may be at least partially transparent. Accordingly, a user of medical device 100 may view the components housed within cassette device 170, such as expandable member 160, through top wall 174. In other embodiments, cassette device 170 may be configured such that bottom wall 172 may be transparent, top wall 174 may be opaque, and/or any other combinations thereof.

A longitudinal length of cassette device 170 is defined by a distal end 176 and a proximal end 178, with proximal end 178 including an opening 184 positioned thereon. Opening 184 may be configured to provide access to one or more channels 180, 182 of cassette device 170. In the example, cassette device 170 may include a first channel 180 and a second channel 182 defined by and formed between the pair of walls 172, 174. First channel 180 may be positioned proximally relative to second channel 182 such that first channel 180 is adjacent proximal end 178 and second channel 182 is adjacent to distal end 176. Further, first channel 180 and second channel 182 may extend relatively parallel to, and be in coaxial alignment with, one another.

Still referring to FIG. 10A, channels 180, 182 of cassette device 170 may include various sizes, shapes, and/or configurations. For example, channels 180, 182 may include a cylindrical, rectangular, oval, square, and/or other suitable profiles. In some embodiments, first channel 180 may have a greater cross-sectional dimension than second channel 182. In the embodiment, cassette device 170 includes a pair of channels 180, 182 for holding a single expandable member 160. In other embodiments, cassette device 170 may include additional channels 180, 182 such that cassette device 170 may be operable to hold multiple expandable members 160 therein. In some embodiments, cassette device 170 may hold multiple expandable members 160 of varying relative sizes and/or shapes.

As described in detail herein, first channel 180 is configured to maintain expandable member 160 in a first compressed state and second channel 182 is configured to maintain expandable member 160 in a second compressed state, with the second compressed state including application of a greater compressing force onto expandable member 160 than the first compressed state. Accordingly, second channel 182 is configured to maintain expandable member 160 in a relatively smaller profile than first channel 180.

According to an exemplary method of using medical device 100, handle 102 may be maneuvered relative to cassette device 170 to align shaft 140 with opening 184. Cassette device 170 may be preloaded with at least one expandable member 160 housed within second channel 182. Distal end 142 may be slidably received within first channel 180 due to a corresponding cross-sectional dimension of shaft 140 and first channel 180. In other words, first channel 180 may be sized in accordance with a size of shaft 140 to facilitate receipt of distal end 142 through opening 186 and into cassette device 170. It should be understood that a size of second channel 182 may be relatively smaller than shaft 140 such that distal end 142 is inhibited from extending into second channel 182.

Actuator 130 may be translated distally along body 104 by moving spool 132 through slot 112 and toward end cap 120. With actuation wire 114 fixed to actuator 130, distal end 116 may translate through lumen 141 (FIG. 4) and extend distally from distal end 142 and cautery device 146. In this instance, engagement assembly 150 may extend outwardly from lumen 141 and be at least partially received in second channel 182.

Figure 10B:
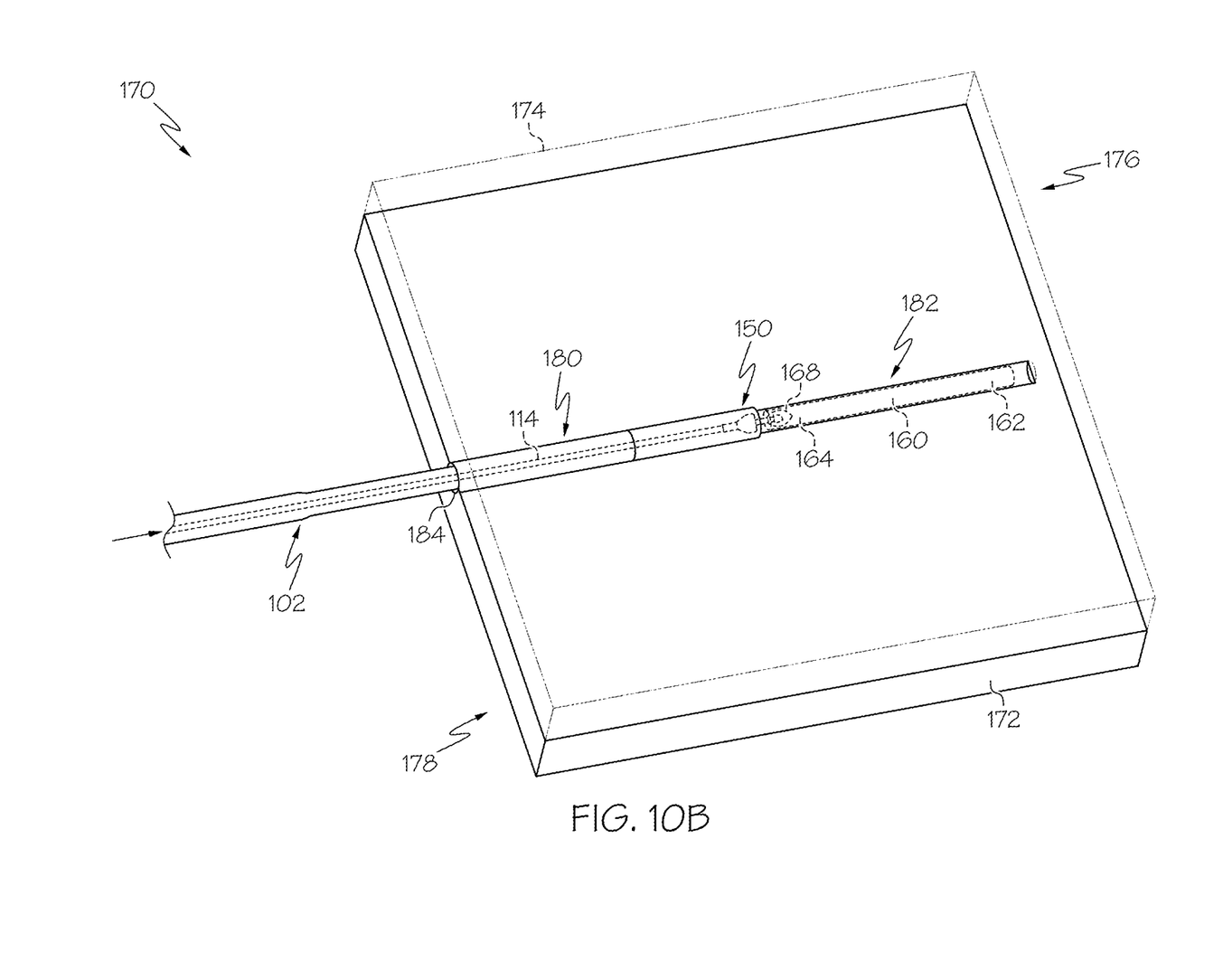
FIG. 10B is a perspective view of the cassette device of FIG. 10A receiving the medical device of FIG. 1 therein, according to aspects of this disclosure.

Referring to FIG. 10B, engagement assembly 150 may engage expandable member 160 when distal tip 156 abuts against proximal end 164 and applies an exerting force against hole 166. In this instance, distal tip 156 may cause hole 166 to expand, thereby accommodating receipt of distal tip 156 therethrough until distal tip 156 is disposed within cavity 168. It should be appreciated that a conical configuration of front face 158 and rear face 157 may facilitate a gradual expansion of hole 166 as distal tip 156 is pushed further into expandable member 160.

As seen in FIG. 9, rear face 157 may be configured to abut against the inner wall defining cavity 168 to secure distal tip 156 therein. Further, rear face 157 may inhibit removal of engagement assembly 150 from expandable member 160 in response to the engagement of the inner wall with rear face 157. Accordingly, a proximal retraction of engagement assembly 150 relative to cassette device 170 may cause distal tip 156 to pull expandable member 160 proximally from second channel 182 and into first channel 180.

Figure 10C:
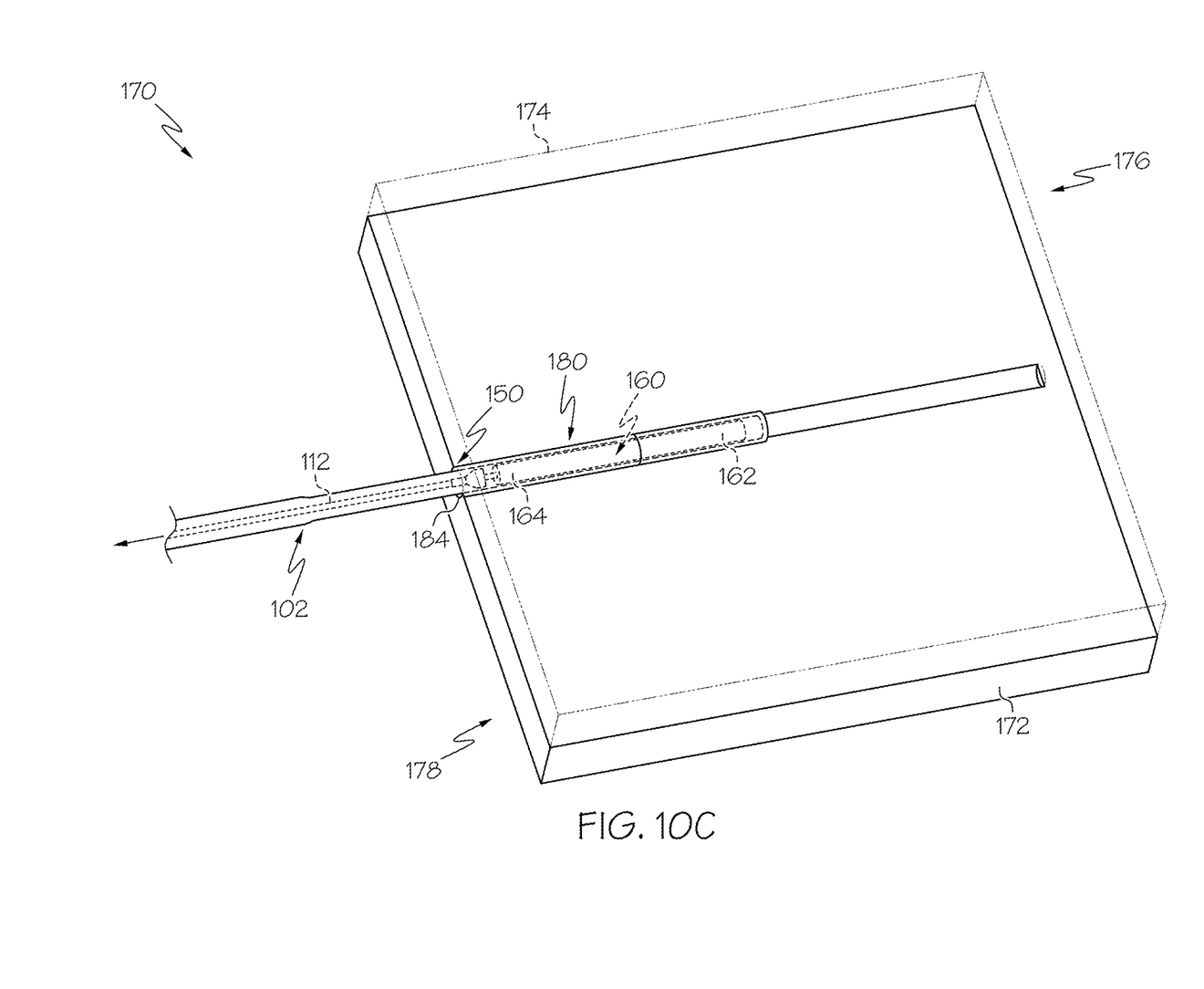
FIG. 10C is a perspective view of the cassette device of FIG. 10A with the medical device of FIG. 1 engaged to the expandable member of FIG. 7 housed therein, according to aspects of this disclosure.

Referring to FIG. 10C, engagement assembly 150 may be retracted into first channel 180 in response to moving handle 102 (and shaft 140) in a proximal direction relative to cassette device 170. In this instance, expandable member 160 may be moved from second channel 182 to first channel 180 and transitioned from the second compressed state to the first compressed state.

With distal end 142 maintained in opening 184 as expandable member 160 is disposed within first channel 180, engagement assembly 150 may be configured to draw expandable member 160 into medical device 100 by actuating actuator 130. For example, in response to moving spool 132 in a proximal direction relative to handle 102, actuation wire 114 may translate proximally within lumen 141, thereby causing engagement assembly 150 to move into shaft 140. With expandable member 160 engaged to engagement assembly 150, expandable member 160 may be simultaneously drawn through cautery device 146 and distal end 142, and received within lumen 141.

It should be appreciated that expandable member 160 may be maintained in a compressed state when received through cautery device 146 and shaft 140. Tapered body 147 may provide clearance for receiving expandable member 160 from first channel 180 in the first compressed state, and tapered section 143 may further compress expandable member 160 as engagement member 150 is retracted further into lumen 141. In other words, due a tapered configuration of tapered body 147 relative to tapered section 143, medical device 100 may be configured to apply an increasing force onto expandable member 160 as actuation wire 114 retracts engagement assembly 150 further into shaft 140. Accordingly, expandable member 160 may be received in shaft 140 and restricted to a compressed state when disposed within lumen 141.

It should be understood that a cross-sectional dimension of lumen 141 may continuously decrease in a proximal-direction along tapered section 143 and tapered body 147. Thus, expandable member 160 may be maintained within lumen 141 at varying extents of compression due to the tapered configuration of tapered section 143 and tapered body 147. For example, proximal end 164 may receive a greater compressing force than distal end 162 when expandable member 160 is disposed within lumen 141.

With expandable member 160 received within shaft 140, medical device 100 may be used in a procedure by inserting shaft 140 into a subject (e.g., patient), such as, for example, via a medical instrument (e.g., an endoscope). Distal end 142 may be positioned at a target site, such as, for example, a perforation, a wound, and/or a cyst located within a gastrointestinal (GI) tract of the subject. In some examples, cautery device 146 may be activated to ablate one or more objects (e.g., tissue) to facilitate access of medical device 100 to the target site. For example, when the target site is a cyst positioned within the pancreas of a subject, cautery device 146 may be activated to create an access opening through an exterior surface of the pancreas to facilitate access to the cyst disposed therein.

In some examples, distal end 142 and/or cautery device 146 may include an echogenic marker to facilitate navigating and/or positioning medical device 100 at the target site. In this instance, as described in detail above, the marker may provide improved visibility of medical device 100 through use of an imaging device, such as, for example an ultrasound machine. Additionally, actuation wire 114 may be articulated (e.g., via actuator 130) when disposed within shaft 140 to facilitate positioning distal end 142 at the target site. Actuator 130 may be actuated (e.g., moved) to deploy expandable member 160 from shaft 140 once distal end 142 is positioned at the target site.

For example, a thumb of a user may be received through the ring of grasping feature 110 and a forefinger and middle finger of the user may be received along spool 132. In this instance, a user may actuate medical device 100 using a single hand on handle 102 by moving the forefinger and middle finger relative to the thumb (or vice versa). Spool 132 may be translated distally relative to handle 102 to extend actuation wire 114 distally through slot 112, thereby extending engagement assembly 150 distally relative to lumen 141.

In this instance, expandable member 160 may move out of lumen 141 via opening 148 (FIG. 6) and be disposed within the target site. Positioning expandable member 160 distally from shaft 140 may remove the compressing force applied thereto, thereby allowing expandable member 160 to transition from a compressed state to an expanded state. Expandable member 160 may contact and absorb fluids in the target site upon deployment from shaft 140. It should be appreciated that expandable member 160 may remain engaged to engagement assembly 150 when extended outwardly from shaft 140 and transitioned to the expanded state.

In some examples, proximal end 118 (FIG. 4) may be coupled to a pressure regulator (e.g., a pump) configured to generate a negative pressure, such as, for example, via a tube received through first opening 105 (FIG. 2). In this instance, activation of the pressure regulator may generate a vacuum through an inner channel of actuation wire 114. With distal end 116 coupled to proximal base 153, and distal tip 156 received within cavity 168, a vacuum may be formed through expandable member 160. Accordingly, fluid (e.g., cystic fluid) absorbed by and/or positioned adjacent to expandable member 160 may be suctioned through expandable member 160 and into actuation wire 114 in response to activation of the pressure regulator.

Expandable member 160 may be disengaged from engagement assembly 150 in response to actuating (e.g., moving) actuator 130. For example, a proximal translation of spool 132 relative to handle 102 may cause actuation wire 114 to move proximally relative to shaft 140, thereby retracting engagement assembly 150 into lumen 141. As a result, proximal end 164 may encounter a distal end of cautery device 146 due to expandable member 160 having an increased cross-sectional dimension in the expanded state.

Continued retraction of actuation wire 114 may cause cautery device 146 to abut against proximal end 164 until distal tip 156 is removed from cavity 168. Accordingly, expandable member 160 may become detached from engagement assembly 150 and deployed at the target site. Expandable member 160 may be biodegradable such that tissue at the target site may absorb expandable member 160 after a predetermined duration (e.g., minutes, hours, days, weeks, etc.). In some examples, expandable member 160 may be preloaded with a therapeutic substance such that the substance may be delivered to the target site while expandable member 160 is deployed therein. Accordingly, expandable member 160 may be operable to provide treatment to the target site in response to absorbing fluids and delivering a therapeutic substance thereto.

With expandable member 160 disengaged from medical device 100 and deployed at the target site, a user may reload medical device 100 with a subsequent expandable member 160 stored in the same and/or an additional cassette device 170. Accordingly, medical device 100 may be configured to deploy multiple expandable members 160 at one or more target sites upon deployment of an initial expandable member 160. For example, expandable member 160 may be absorbed by the surrounding tissue within the target site after a predetermined biodegradation duration (e.g., one or more days) such that a subsequent expandable member 160 may be deployed at the target site during a therapy procedure.

Alternatively, a user may exchange a deployed expandable member 160 with a subsequent expandable member 160 after a predetermined duration (e.g., 2-5 days) to continue treatment of the target site. In examples where the target site is a perforation having a leak, the subsequent expandable member 160 may include a relatively smaller size (or different shape) than a previously deployed expandable member 160 due to size of the perforation continuously decreasing during the therapy procedure.

Each of the aforementioned systems, devices, assemblies, and methods may be used to treat a perforation, wound, or cyst by deploying an expandable member (e.g., a foam) capable of absorbing fluids and delivering therapeutic substances thereto. By providing a medical device with an intuitive handle interface capable of controlling a loading and unloading of an expandable member with a single hand, a user may utilize another hand to control other devices and/or tools during a procedure for treating the target site. In this instance, a user may reduce overall procedure time, increase efficiency of procedures, and/or avoid unnecessary harm to a subject's body caused by limited control of the other tools/devices.

It will be apparent to those skilled in the art that various modifications and variations may be made in the disclosed devices and methods without departing from the scope of the disclosure. It should be appreciated that the disclosed devices may include various suitable computer systems and/or computing units incorporating a plurality of hardware components, such as, for example, a processor and non-transitory computer-readable medium, that allow the devices to perform one or more operations during a procedure in accordance with those described herein. Other aspects of the disclosure will be apparent to those skilled in the art from consideration of the specification and practice of the features disclosed herein. It is intended that the specification and examples be considered as exemplary only.

We claim:

1. A medical device, comprising:
a handle;
a shaft extending distally from the handle and defining a lumen;
an actuator disposed in the shaft and including a distal tip, wherein the actuator and the distal tip are movable relative to the lumen;
an expandable member having an inner cavity; and
a cautery device extending distally from the shaft, wherein the cautery device is configured to cauterize tissue, wherein the cautery device defines an inner channel that is tapered such that a dimension of the inner channel increases distally from the shaft, and wherein the actuator is configured to engage the expandable member when moving distally relative to the lumen and in response to the distal tip entering the inner cavity, and disengage the expandable member when moving proximally relative to the lumen and in response to the distal tip exiting the inner cavity.

2. The medical device of claim 1, wherein a distal portion of the shaft is tapered such that a dimension of the lumen increases at the distal portion.

3. The medical device of claim 1, further including an actuator body movably coupled to an exterior of the handle and disposed over a slot of the handle.

4. The medical device of claim 3, wherein a proximal portion of the actuator is received within the slot and fixed to the actuator body such that translation of the actuator body relative to the slot is configured to move the actuator relative to the lumen of the shaft.

5. The medical device of claim 4, wherein the shaft is configured to receive the expandable member within the lumen when the distal tip is received within the inner cavity and the actuator is moved proximally relative to the lumen.

6. The medical device of claim 5, wherein a distal portion of the shaft is configured to maintain the expandable member in a compressed state, and permit the expandable member to transition to an expanded state in response to the actuator moving distally relative to the lumen and the expandable member extending outward from the shaft.

7. The medical device of claim 5, wherein a distal portion of the shaft is configured to remove the distal tip from the inner cavity in response to the distal portion of the shaft engaging a proximal end of the expandable member when the actuator moves proximally relative to the lumen.

8. The medical device of claim 1, wherein the expandable member includes an opening such that the inner cavity is accessible via the opening.

9. The medical device of claim 8, wherein the opening is configured to expand when the distal tip is received within the opening.

10. The medical device of claim 1, wherein the actuator includes an inner channel extending between a proximal end and the distal tip.

11. The medical device of claim 10, further including a negative pressure source coupled to the proximal end of the actuator and in fluid communication with the distal tip through the inner channel; and wherein the negative pressure source is configured to generate a negative pressure through the inner channel such that fluid positioned adjacent to the expandable member is drawn through the expandable member and into the inner channel via the distal tip.

12. The medical device of claim 1, further including a cassette including a first channel and a second channel, wherein the cassette is configured to hold the expandable member in the second channel.

13. The medical device of claim 12, wherein the first channel is in coaxial alignment with the second channel and includes a diameter greater than the second channel.

14. The medical device of claim 13, wherein the cassette is configured to receive the shaft within the first channel and the distal tip within the second channel; and wherein the cassette is configured to inhibit the shaft from extending into the second channel.

15. The medical device of claim 1, wherein the cautery device includes an echogenic marker.

16. A medical device, comprising:

a handle having a movable actuator body;
a shaft extending distally from the handle;
an actuator wire disposed within the shaft; and
a cassette including a first channel and a second channel, wherein the cassette is configured to hold an expandable member in the second channel, wherein the movable actuator body is configured to translate the actuator wire out of the shaft to insert the actuator wire into the expandable member, when the actuator wire moves along the handle in a first direction; and wherein the movable actuator body is configured to translate the actuator wire into the shaft to remove the actuator wire from inside the expandable member, when the actuator wire moves along the handle in a second direction that is opposite of the first direction.

17. The medical device of claim 16, wherein the shaft is configured to receive the expandable member in a compressed state when the actuator wire is inserted into the expandable member and the movable actuator body is moved in the second direction.

18. The medical device of claim 16, further including a cautery device extending distally from the shaft, wherein the cautery device is configured to generate heat to cauterize tissue.

19. The medical device of claim 16, wherein the cassette is configured to receive the shaft within the first channel and the actuator wire within the second channel; and wherein the cassette is configured to inhibit the shaft from extending into the second channel.

20. A medical device, comprising:

a handle;
a shaft extending distally from the handle; and
an actuator including a wire disposed within the shaft; and
a cassette including a channel housing an expandable member;

wherein the actuator is configured to extend the wire outwardly from the shaft and into the cassette to engage the expandable member within the channel, when the actuator moves distally over the shaft; and wherein the actuator is configured to retract the wire into the shaft and outward from the cassette to remove the expandable member from the channel, when the actuator moves proximally over the shaft.

* * * * *